(12) United States Patent
Netsch et al.

(10) Patent No.: US 9,020,234 B2
(45) Date of Patent: Apr. 28, 2015

(54) CONTOUR DELINEATION FOR RADIATION THERAPY PLANNING WITH REAL-TIME CONTOUR SEGMENT IMPACT RENDERING

(75) Inventors: Thomas Netsch, Hamburg (DE); Daniel Bystrov, Hamburg (DE)

(73) Assignee: Koninklijke Philips N.V., Eindhoven (NL)

( * ) Notice: Subject to any disclaimer, the term of this patent is extended or adjusted under 35 U.S.C. 154(b) by 278 days.

(21) Appl. No.: 13/821,572

(22) PCT Filed: Sep. 5, 2011

(86) PCT No.: PCT/IB2011/053864
§ 371 (c)(1),
(2), (4) Date: Mar. 8, 2013

(87) PCT Pub. No.: WO2012/035463
PCT Pub. Date: Mar. 22, 2012

(65) Prior Publication Data
US 2013/0301893 A1 Nov. 14, 2013

Related U.S. Application Data

(60) Provisional application No. 61/383,780, filed on Sep. 17, 2010.

(51) Int. Cl.
*G06T 7/00* (2006.01)
*A61N 5/10* (2006.01)

(52) U.S. Cl.
CPC .............. *G06T 7/0012* (2013.01); *A61N 5/103* (2013.01); *G06T 7/0083* (2013.01); *G06T 2207/10072* (2013.01); *G06T 2207/30096* (2013.01)

(58) Field of Classification Search
CPC .............. G06T 7/0012; G06T 7/0083; G06T 2207/10072; G06T 2207/30004; G06T 2207/30096; G06K 2209/05; G06K 2209/051; A61N 5/103; A61N 5/1048; A61N 2005/1074; A61B 6/46; A61B 6/461; A61B 6/52; A61B 6/5205
See application file for complete search history.

(56) References Cited

U.S. PATENT DOCUMENTS

| 6,249,594 B1 | 6/2001 | Hibbard | 382/128 |
| 7,693,257 B2 | 4/2010 | Allison | 378/65 |

(Continued)

FOREIGN PATENT DOCUMENTS

| WO | 9940523 A1 | 8/1999 | G06F 17/18 |
| WO | 2008120116 A1 | 10/2008 | A61N 5/10 |

(Continued)

*Primary Examiner* — Andrew W Johns (57) ABSTRACT

A contouring module (22, 24) iteratively adjusts contours delineating a radiation target region and risk regions in a planning image. An intensity modulation optimization module (30) generates a radiation therapy plan conforming with dosage or dosage constraints (26) for the radiation target region and the risk regions delineated by the contours. A differential analysis module (40) is configured to invoke the intensity modulation optimization module (30) to estimate partial derivatives of an output of the intensity modulation optimization respective to the contours. The contouring module (22, 24) is configured to invoke the differential analysis module (40) after each iterative contour adjustment to estimate the partial derivatives respective to the contour segments and to render the contour segments on a display of the planning image with the contour segments coded based on the estimated partial derivatives to indicate impact of the contour segments on the intensity modulation optimization.

20 Claims, 6 Drawing Sheets

(56) References Cited

U.S. PATENT DOCUMENTS

| | | | |
|---|---|---|---|
| 7,708,682 B2 | 5/2010 | Pekar et al. | 600/1 |
| 2004/0022438 A1 | 2/2004 | Hibbard | 382/199 |
| 2007/0211939 A1* | 9/2007 | Kaus et al. | 382/173 |
| 2007/0230765 A1 | 10/2007 | Wang et al. | 382/132 |
| 2014/0201670 A1* | 7/2014 | Mallya et al. | G06T 7/0012 |

FOREIGN PATENT DOCUMENTS

| | | | |
|---|---|---|---|
| WO | 2010025372 A2 | 3/2010 | A61B 6/00 |
| WO | 2010079394 A1 | 7/2010 | G06T 7/00 |

* cited by examiner

CONTOUR DELINEATION FOR RADIATION THERAPY PLANNING WITH REAL-TIME CONTOUR SEGMENT IMPACT RENDERING

CROSS REFERENCE TO RELATED APPLICATIONS

This application is a national filing of PCT application Serial No. PCT/IB2011/053864, filed Sep. 5, 2011, published as WO 2012/035463 A1 on Mar. 22, 2012, which claims the benefit of U.S. provisional application Ser. No. 61/383,780 filed Sep. 17, 2010, which is incorporated herein by reference.

The following relates to the radiation therapy arts, medical arts, radiation therapy planning arts, image processing arts, and related arts.

In radiation therapy, spatially targeted dosages of ionizing radiation are applied to a tumor or other region containing cancerous or malignant tissue. Growing and rapidly multiplying cancer cells tend to be more susceptible to damage from ionizing radiation as compared with normal cells, and so enforced by the higher dosage administrated by proper planning the applied radiation preferentially kills cancerous or malignant tissue. Nonetheless, ionizing radiation is harmful to both malignant and healthy cells, and so precise spatial targeting of the radiation is important for applying effective radiation therapy to the malignancy while limiting collateral damage to healthy tissue.

In radiation therapy, the radiation beam .is applied at angular positions around the subject in a manner that-combines to produce a targeted total radiation dosage spatial distribution that is concentrated on the tumor or other region to be treated, while keeping the integrated exposure of certain radiation-sensitive critical organs below a safety threshold. Angular coverage can be achieved by using a. plurality of stationary radiation sources distributed around the subject, or by revolving a single radiation source such as a linear accelerator (linac) around the subject (i.e., tomotherapy). The radiation therapy is planned in advance for a specific subject, based on imaging data acquired of that subject. Typically, computed tomography (CT) imaging is used for radiation therapy planning, although other imaging modalities such as magnetic resonance (MR) or positron emission tomography (PET) may also be utilized additionally to or instead of CT.

To plan the radiation therapy session, the tumor or other target is delineated in the images, along with delineation of radiation-sensitive "risk" organs or regions whose radiation dosage must be limited. Radiation plan parameters are provided by the oncologist or other medical personnel. The radiation therapy plan parameters typically include a minimum or target dose to be delivered to the malignant tumor, and maximum permissible dosages for the risk organs or regions. The organ delineations together with the radiation therapy plan parameters and known information about radiation attenuation or absorption characteristics of the various tissues serve as inputs to an intensity modulation optimization that optimizes the radiation beam spatial profile and intensities to concentrate the radiation in the target while limiting exposure of risk organs or regions so as to satisfy the radiation therapy plan parameters. One known radiation therapy planning system for performing such image guided radiation therapy is the Pinnacle™ radiation therapy planning system (available from Koninklijke Philips Electronics N.V., Eindhoven, the Netherlands).

Conventionally, the intensity modulation optimization has been a substantial bottleneck in the radiation therapy workflow. The optimization is an "inverse" process, in which the radiation beam spatial profile and intensities are optimized to provide an optimized radiation dose map computed based on these spatial profiles and intensities. However, this bottleneck is gradually being alleviated by the increased processing speed provided by newer computers.

The contouring process is also a workflow bottleneck. Precise delineation of the tumor and all relevant risk organs is generally considered to be a critical aspect of the radiation therapy planning process. To ensure accuracy and precision, the contouring is performed manually by a radiologist or other trained medical personnel. Some systems provide an automated segmentation for defining the initial contours—however, in such systems there is usually a subsequent manual contouring operation in which the radiologist or other trained medical personnel verify and adjust, as appropriate, the contours. The manual contouring process is tedious and time-consuming, and ties up valuable time of professional medical personnel.

The following provides a new and improved apparatuses and methods which overcome the above-referenced problems and others.

In accordance with one disclosed aspect, a method comprises: performing contouring to define contours delineating a radiation target region and one or more risk regions in a planning image; and during the contouring, displaying a planning image and the contours, the displaying including coding the contours to indicate impact of the contours on an output of an intensity modulation optimization.

In accordance with another disclosed aspect, a method comprises: performing contouring to define contour segments delineating a radiation target region and one or more risk regions in a planning image; performing intensity modulation optimization using the contour segments to generate a radiation therapy plan and a corresponding calculated radiation dose map; and during the contouring, displaying the planning image and the contour segments with the contour segments coded with respect to impact of the contour segments on the intensity modulation optimization.

In accordance with another disclosed aspect, a method comprises: calculating a radiation dose map complying with dose plan parameters indicative of dosage or dosage constraints for a radiation target region and one or more risk regions by an intensity modulation optimization having as input at least contours delineating the radiation target region and the one or more risk regions; and rendering the contours on a displayed planning image including coding the contours to indicate impact of the contours on the intensity modulation optimization.

In accordance with another disclosed aspect, a digital processor configured to perform a method as set forth in any one of the immediately preceding three paragraphs is disclosed. In accordance with another disclosed aspect, a storage medium is disclosed which stores instructions executable by a digital processor to perform a method as set forth in any one of the immediately preceding three paragraphs.

In accordance with another disclosed aspect, an apparatus comprises: a contouring module configured to iteratively adjust contours delineating a radiation target region and one or more risk regions in a planning image; an intensity modulation optimization module configured to generate a radiation therapy plan conforming with dosage or dosage constraints for the radiation target region and the one or more risk regions delineated by the contours; and a differential analysis module configured to invoke the intensity modulation optimization module to estimate partial derivatives of an output of the intensity modulation optimization respective to the contours;

wherein the contouring module is configured to invoke the differential analysis module after each iterative contour adjustment to estimate the partial derivatives respective to the contour segments and to render the contour segments on a display of the planning image with the contour segments coded based on the estimated partial derivatives to indicate impact of the contour segments on the intensity modulation optimization.

One advantage resides in providing more efficient contouring for radiation therapy planning.

Another advantage resides in providing feedback to the radiologist or other medical professional during radiation therapy planning.

Another advantage resides in providing a radiologist or other medical professional with guidance during contouring for radiation therapy planning.

Further advantages will be apparent to those of ordinary skill in the art upon reading and understand the following detailed description.

Figure 1:
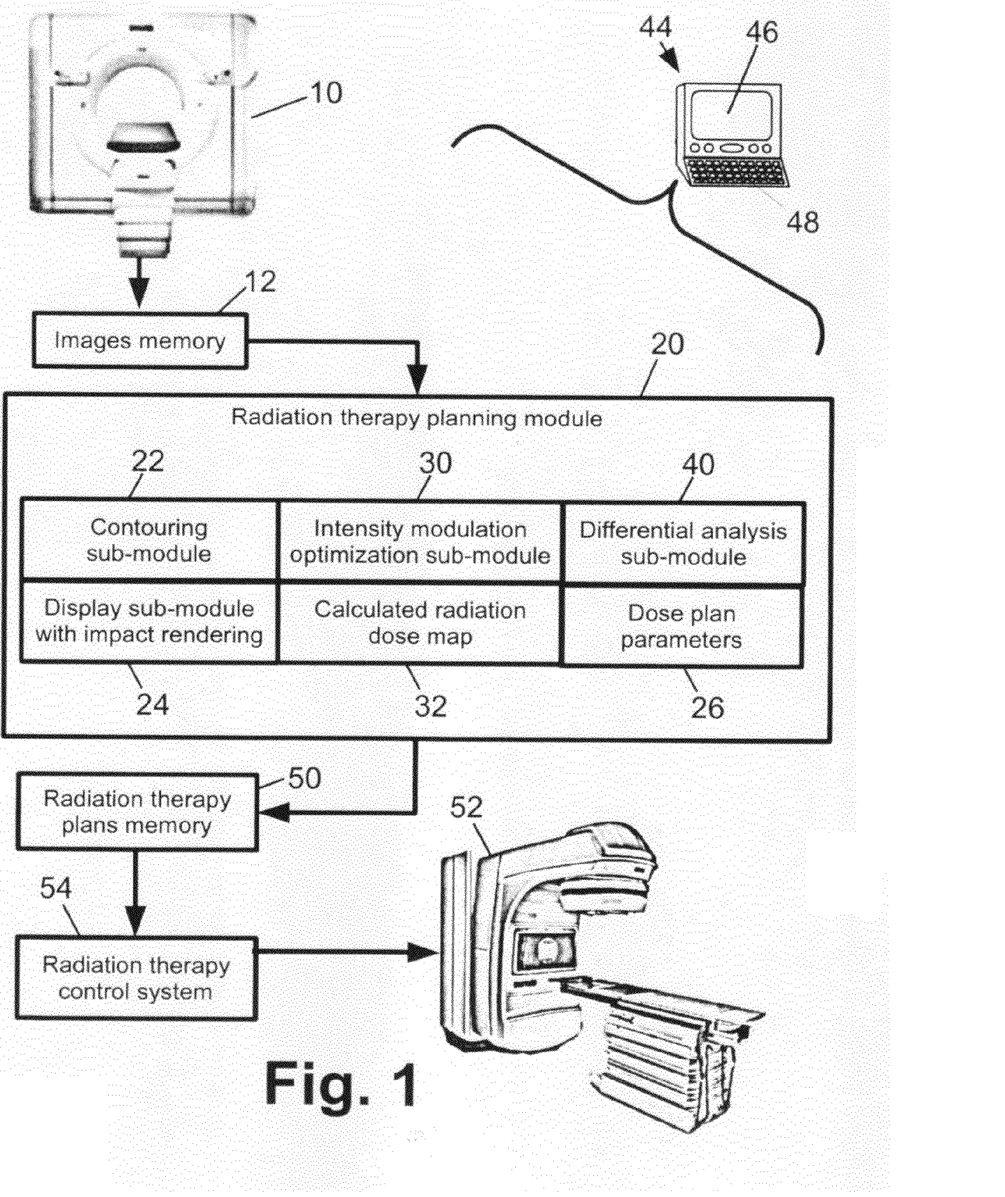
FIG. 1 diagrammatically shows a radiation therapy system including a radiation therapy planning module.

With reference to FIG. 1, a radiation therapy system includes an imaging modality 10 suitable for acquiring a planning image for planning radiation therapy. In some embodiments, the imaging modality 10 is a computed tomography (CT) scanner, such as the Brilliance™ Big Bore™ CT scanner (available from Koninklijke Philips Electronics N.V., Eindhoven, the Netherlands). The Brilliance™ Big Bore™ CT scanner is an illustrative CT scanner having a large 85 cm patient aperture that is large enough to accommodate the patient arranged in typical radiation therapy positions. Other CT scanners can be used instead, as well as other imaging modalities such as positron emission tomography (PET), magnetic resonance (MR), single photon emission computed tomography (SPECT), or so forth. Acquired images are stored in an images memory 12. The planning image is preferably acquired of the subject scheduled to undergo the radiation therapy. For example, the subject may be an oncology patient, or a veterinary subject, or so forth. The term "planning image" in this context relates to the planning image (or set of planning images) used for the contouring.

Prior to the radiation therapy session, a radiation therapy planning module 20 performs radiation therapy planning. The planning module 20 includes a contouring sub-module 22 and a display sub-module 24 that cooperate to perform contouring to define contours delineating a radiation target region and one or more risk regions in the planning image. For example, the radiation target region may be a cancerous tumor, and the one or more risk regions may include neighboring vital organs or tissue whose radiation exposure should be kept below a maximum value. Toward this end, the radiation therapy planning is respective to dose plan parameters 26 that are indicative of dosage or dosage constraints for the radiation target region and the one or more risk regions.

An intensity modulation optimization sub-module 30 receives as input at least the contours generated by the delineating contouring components 22, 24, and generates a radiation therapy plan and a calculated radiation dose map 32 complying with the dose plan parameters 26. The intensity modulation optimization sub-module 30 optionally receives other relevant inputs, such as an attenuation map indicative of radiation absorption (for example, suitably computed based on the planning image and/or an anatomical model). The intensity modulation optimization is typically an iterative "inverse" process in which: (1) radiation therapy parameters such as beam intensities, collimator settings, or so forth are initialized followed by (2) computing a calculated dose map using these parameters followed by (3) assessing compliance of the calculated dose map with the dose plan parameters 26 followed by (4) update of the radiation therapy parameters in a way expected to bring the calculated dose map closer to compliance with the dose plan parameters 26. Operations (2)-(4) are then repeated to iteratively bring the calculated dose map into optimal compliance with the dose plan parameters 26.

During the contouring performed by the contouring components 22, 24, the display sub-module 24 renders the contours with coding (for example, color coding and/or line thickness coding) indicative of the impact of the contours on the intensity modulation optimization. Toward this end, a differential analysis sub-module 40 is configured to invoke the intensity modulation optimization sub-module 30 to estimate partial derivatives of an output of the intensity modulation optimization respective to the contours. In some embodiments, the output of the intensity modulation optimization is the dose distribution, each partial derivative quantifies how the dose deposit is changing when the contour point or segment changes, and the partial derivative quantifies the change with respect to the dose deposit at a contour segment, or the derivative with respect to the dose distribution at a contour position. The contouring sub-module 22 is configured to invoke the differential analysis sub-module 40 after each iterative contour adjustment to estimate the partial derivatives respective to the contour segments and to render the contour segments on a display of the planning image with the contour segments coded based on the estimated partial derivatives to indicate impact of the contour segments on the intensity modulation optimization.

In one approach, the radiation therapy planning module 20 is implemented on a suitable computer 44 having a display device 46 (for example, an LCD screen, a cathode ray tube display device, or so forth) and one or more user input devices such as an illustrative keyboard 48, or a mouse, trackball, or other pointing user input device, or so forth. The display sub-module 24 displays the planning image on the display device 46 with the contour segments coded based on the estimated partial derivatives to indicate impact of the contour segments on the intensity modulation optimization. A user manually inputs an adjustment of a contour via the user input device 48. The contouring sub-module 22 then invokes the differential analysis sub-module 40 to estimate the partial derivatives respective to the contours, including the adjusted contour, and to render the (updated) contour segments on the display device 46 superimposed on the planning image and coded to indicate (updated) impact of the contour segments on the intensity modulation optimization.

The final radiation therapy plan generated by the radiation therapy planning module 20 is stored in a radiation therapy plans memory 50. At the scheduled day and time for the radiation therapy session, a radiation therapy apparatus 52 is employed to deliver therapeutic radiation to the subject controlled by a radiation therapy control system 54 in accordance with the radiation therapy plan stored in the memory 50. For example, in the illustrated embodiment the radiation therapy delivery apparatus 52 is a tomographic linear accelerator (linac), and the radiation therapy control system 54 operates multileaf collimator (MLC) or other radiation beam profile-shaping apparatus of the linac 52 to modulate beam intensity and profile as the linear accelerator is revolved around the subject, so as to deliver a radiation dose distribution into the subject that provides the desired integrated radiation dosage to the target feature while suitably limiting or constraining radiation exposure of sensitive critical features in accordance with the radiation therapy plan which complies with the dose plan parameters 26.

The radiation therapy planning module 20 can be variously embodied by a single digital processor, a two or more digital processors, computers, application-specific integrated circuitry (ASIC), or so forth. For example, the illustrated computer 44 can embody the planning module 20. Similarly, the radiation therapy planning including contouring with coding of the contours as to impact on the intensity modulation optimization may be embodied by a storage medium storing instructions executable by a digital processor to perform the planning including contouring with contour coding. For example, the storage medium may be a hard disk or other magnetic storage medium, an optical disk or other optical storage medium, a random access memory (RAM), read-only memory (ROM), FLASH memory, or other electronic storage medium, various combinations thereof, or so forth.

Figure 2:
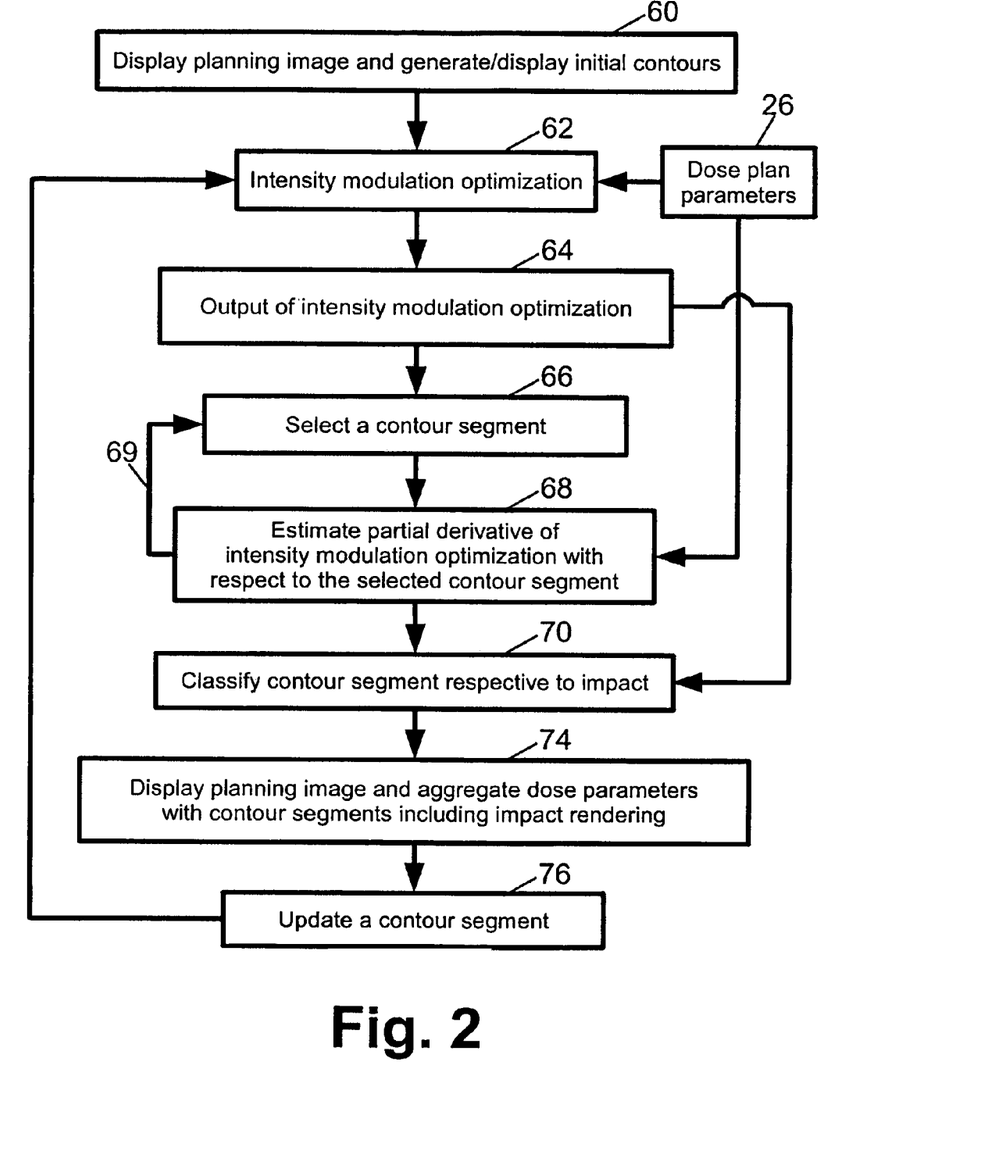
FIG. 2 diagrammatically shows a radiation therapy planning method suitably performed by the radiation therapy planning module of the system of FIG. 1.

With reference to FIG. 2, an illustrative radiation therapy planning method including contouring with coding of the contours as to impact on the intensity modulation optimization, suitably performed by the system of FIG. 1, is described. In an operation 60, the planning image is displayed and initial contours are generated and displayed. The operation 60 can employ manual initial contouring, automatic initial contouring utilizing automatic segmentation of the planning image, or a semi-automatic approach. An intensity modulation optimization operation 62 is then performed by the intensity modulation optimization sub-module 30, which generates an output 64 including the optimized radiation therapy parameters (e.g., beam intensities, multileaf collimator settings, or so forth), the calculated radiation dose map 32 (see FIG. 1), and optionally additional parameters such as relevant aggregate dosage parameters. For example, the aggregate dose parameters may include the integrated radiation dosage delivered to the radiation target region and/or to one or more risk regions, with each such integrated radiation dosage being computed by integration over the region in the calculated radiation dose map 32. The output 64 may also optionally include one or more synthetic parameters, such as by way of illustrative example a metric indicative of maximum deviation of any calculated region dose (either the radiation target region or a risk region) from a corresponding dose plan parameter.

The calculation of the impact of the contours on the intensity modulation optimization follows in operations 66, 68, 70. To perform the differential analysis, the contours are segmented into contour segments, and partial derivatives are calculated for an output of an intensity modulation optimization respective to the contour segments. Thus, in the operation 66 a contour segment is selected for differential analysis. In the operation 68, the partial derivative is estimated for the output of an intensity modulation optimization respective to the selected contour segment. Operations 66, 68 iterate 69 over all contour segments to estimate the partial derivatives respective to the contour segments. The operation 70 classifies each contour segment respective to its impact on the intensity modulation optimization based on the estimated partial derivatives.

In an operation 74, the display sub-module 24 displays the planning image, optionally displays. selected aggregate dose parameters, and displays the contour segments. including impact rendering, that is, including contour segment coding indicative of impact of the contours on an output of an intensity modulation optimization. This impact is suitably quantified by the contour segment classifications output by the operation 70. In an operation 76 a contour segment is updated. The contour segment update operation 76 may be manual, for example by receiving a contour segment adjustment input by a user via the user input device 48. Alternatively, the contour segment update operation 76 may be automated, for example performed based on a re-segmentation of the radiation target region and/or a risk region in the planning image. Process flow then goes back to the operation 62 to update the calculated radiation dose map 32 and other output 64 of the intensity modulation optimization to take into account the contour segment adjustment, and to update the impact analysis by repeating operations 66, 68, 70, and to update the display, as per the operation 74. In this way, the user observes the impact of contouring operations substantially in real-time, that is, during the contouring process.

Figure 3:
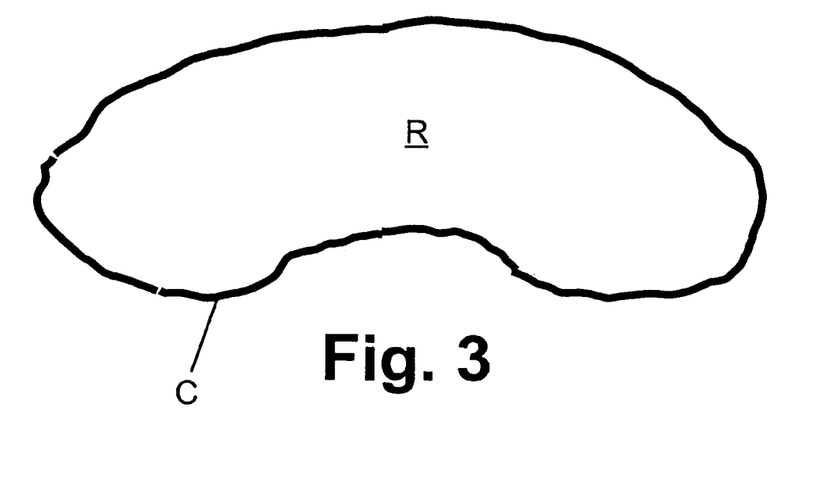
FIGS. 3-6 diagrammatically show a region and delineating contour that diagrammatically show selected operations of the method of FIG. 2.
Figure 4:
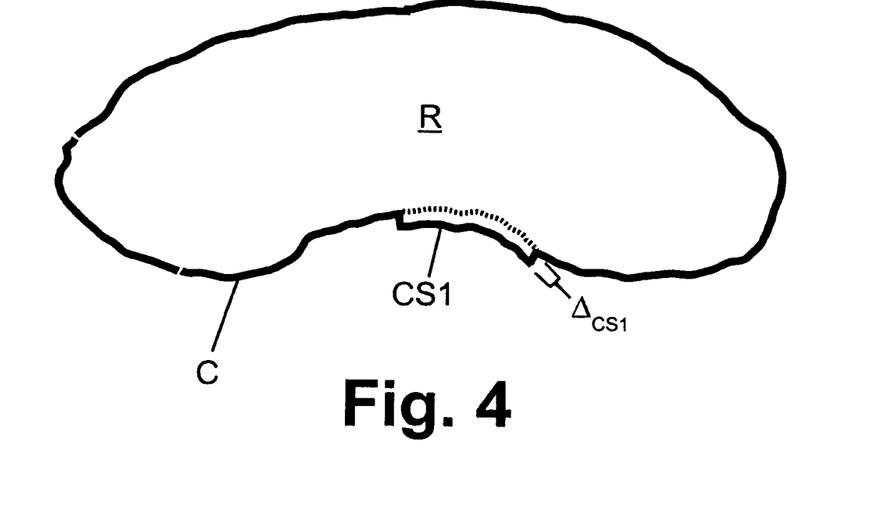

With reference to FIGS. 3-6, the impact analysis performed by the operations 66, 68, 70 of the method of FIG. 2 is diagrammatically illustrated. FIG. 3 illustrates a region R that is delineated by a contour C. The operation 62 computed the output 64 of the intensity modulation optimization for the contour C. For expository purposes, the output 64 (or component thereof that is used for the impact analysis) is referred to here, without loss of generalization, as output Y. FIG. 4 illustrates the region R and the contour C, but with the contour adjusted in that a first selected contour segment CS1 is adjusted outward by a differential amount $\Delta_{CS1}$. (Alternatively, the differential contour segment adjustment could be an inward adjustment). The operation 68 suitably estimates the partial derivative with respect to the first contour segment CS1 by applying the intensity modulation optimization to the adjusted contour to generate an adjusted output $Y_1$ and computing the partial derivative respective to the first contour segment CS1 as $(Y_1-Y)/\Delta_{CS1}$.

Figure 5:
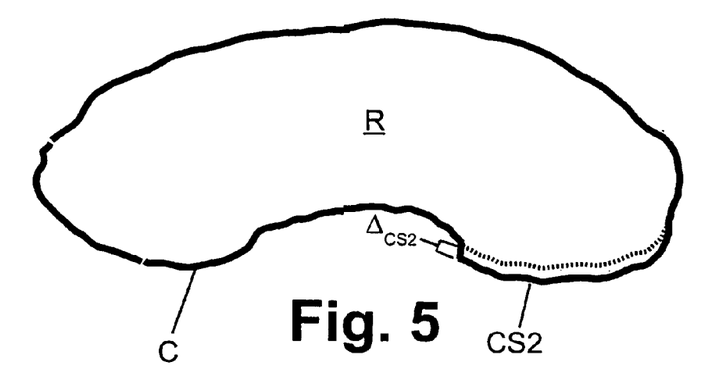

FIG. 5 illustrates the region R and the contour C, but with the contour adjusted in that a second selected contour segment CS2 is adjusted outward by a differential amount $\Delta_{CS2}$. (Again, alternatively the differential contour segment adjustment could be an inward adjustment). This corresponds to the second iteration 69 returning flow to the selection operation 66 which now selects the second contour segment CS2. The second repetition of the operation 68 estimates the partial derivative with respect to the second contour segment CS2 by applying the intensity modulation optimization to the adjusted contour to generate an adjusted output $Y_2$ and computing the partial derivative respective to the second contour segment CS2 as $(Y_2-Y)/\Delta_{CS2}$. (Note that if the differentials used for the contour segments are the same, that is $\Delta CS1=\Delta_{CS2}$ and so forth for all the contour segments, then the scaling by dividing by $\Delta_{CS1}$ or $\Delta_{CS2}$ is optionally omitted).

Figure 6:
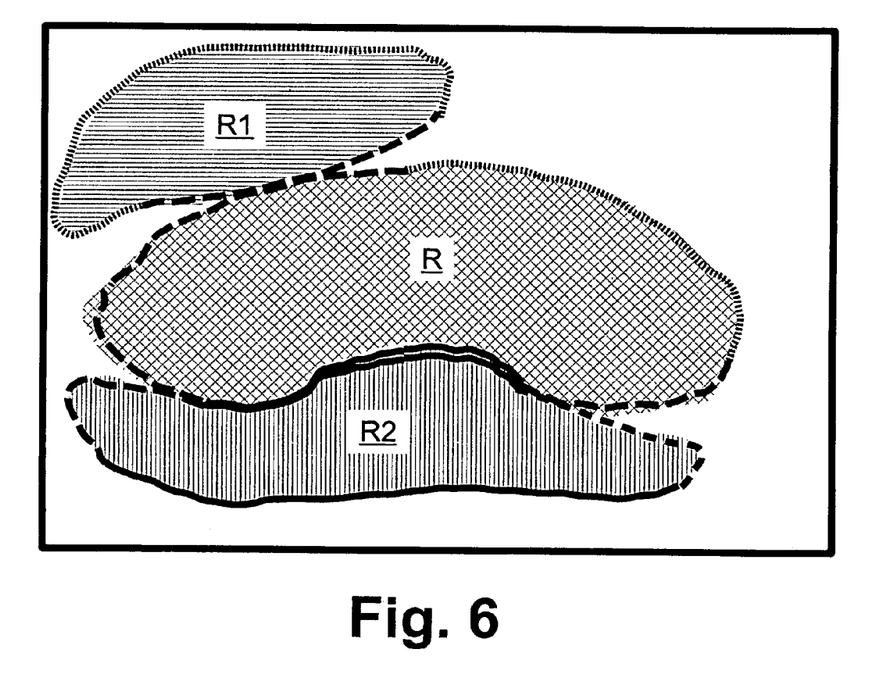

The process is repeated for each contour segment of the contour C by operation of the iterative loop 69 to compute the partial derivatives respective to the contour segments that make up the contour C. In general, the output Y can be any output of the intensity modulation optimization for which the impact of the contouring is of interest. In one example, the output Y can be the dosage in the radiation target region. In another example, the output Y can be a synthetic parameter such as a maximum ratio (over all risk regions) of the dosage in a risk region ratioed against the dosage constraint for that risk region. In the operation 70, the contour segments are classified based on the partial derivatives. For example, in one approach a binary classifier is used, with a contour segment being classified as "high impact" if the partial derivative respective to that contour segment is larger than a threshold value, and classified as "low impact" if the partial derivative respective to that contour segment is below the threshold value. More generally, the classification can be over two classes, three classes, or so forth. In some embodiments, the classification operation 70 is replaced by a continuous scoring operation that assigns a score to each contour segment.

As diagrammatically illustrated in FIG. 6, each contour segment is displayed with a suitable coding indicative of its impact as computed by the classification (or scoring) operation 70. In the illustrative embodiment three impact classes are used. A solid contour line is used to code a high impact segment. A dashed line is used to code a moderate impact segment. A dotted line is used to code a low impact segment. FIG. 6 illustrates such contour coding for the illustrative region R whose impact analysis was described with reference to FIGS. 3-5, as well as for two other regions R1, R2. Although a solid/dashed/dotted line coding is used in FIG. 6, in other embodiments in which the display device 46 is capable of generating a color display the coding may be a color coding, for example employing the color "red" to code for a high impact contour segment, the color "yellow" to code for a moderate impact contour segment, and the color "green" to code for a low impact contour segment.

The coding of the contour segments to indicate impact of the contour segments on the intensity modulation optimization advantageously informs the radiologist or other medical person performing the contouring of which contour segments have the most impact on the intensity modulation optimization. With reference to FIG. 6, for example, the radiologist knows that the contour segments coded with dotted lines have low impact on the intensity modulation optimization, and accordingly the contouring of those dotted contour segments can be done in a relatively coarse fashion. On the other hand, the radiologist knows that the contour segments coded with solid lines have high impact on the intensity modulation optimization, and accordingly the contouring of those solid contour segments should be done with a high degree of care and precision. By informing the radiologist of which contour segments have a high impact and which have a low impact, the contouring process is expedited (by allowing the radiologist to more coarsely position the low impact contour segments) and is also made more accurate (since the radiologist ensures the accuracy of the high impact contour segments).

Figure 7:
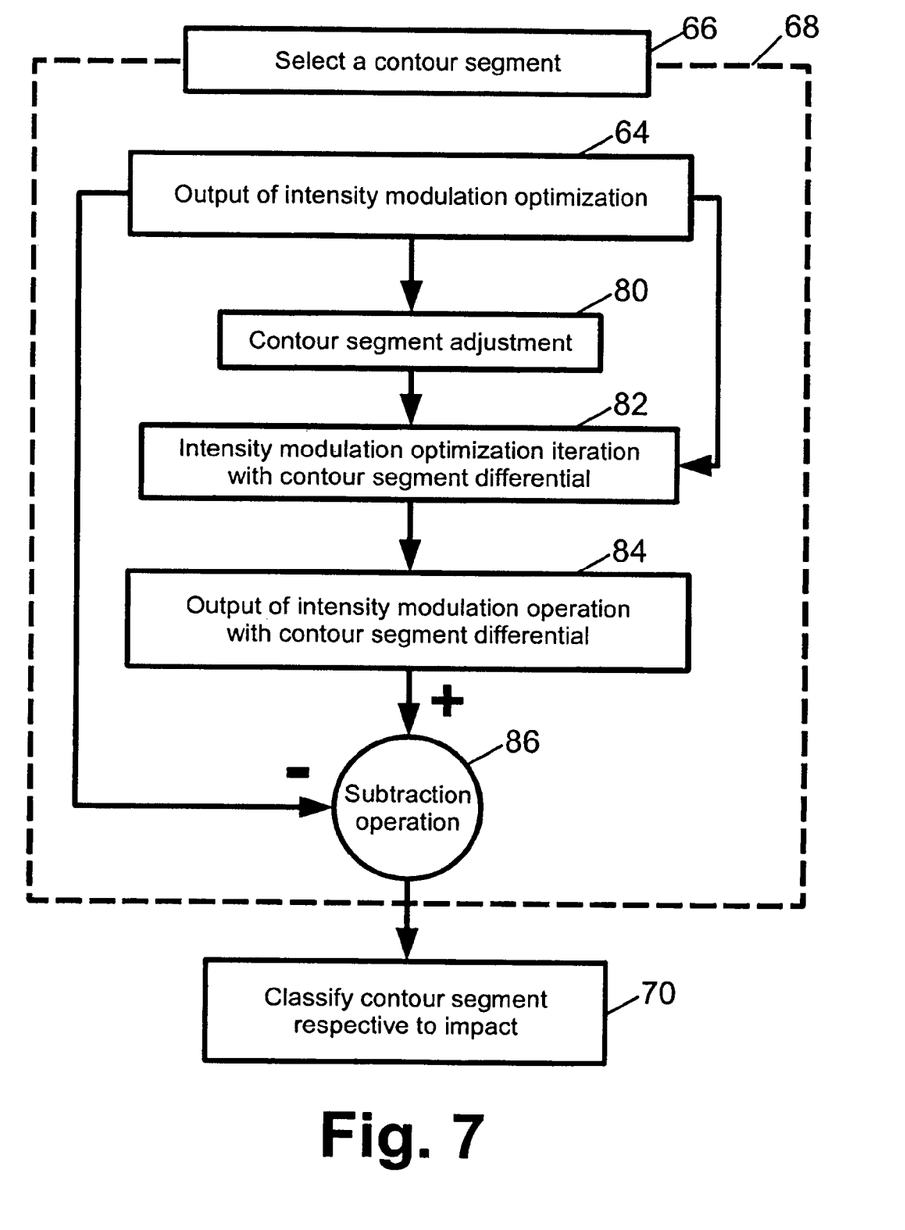
FIG. 7 diagrammatically shows an embodiment of the partial derivative estimation operation of the method of FIG. 2.

With continuing reference to FIGS. 1 and 2 and with further reference to FIG. 7, the partial derivative estimation operation 68 performed by the differential analysis sub-module 40 with invocation of the intensity modulation optimization 30 sub-module 30 can be performed efficiently. This is because the optimization for each partial derivative estimation does not start ab initio, but rather can be performed using the output 64 of the intensity modulation optimization operation 62 as a starting value. As diagrammatically shown in FIG. 7, the partial derivative estimation operation 68 for a contour segment selected in the operation 66 starts with an operation 80 which adjusts the selected contour segment outward (or, in another embodiment, inward) by a differential amount $\Delta_{CS}$ (for example, differential adjustment $\Delta_{CS1}$ in FIG. 4, or differential adjustment $\Delta_{CS2}$ in FIG. 5). In an operation 82, an intensity modulation optimization iteration is performed with the contour segment differential of operation 80 in order to generate an output 84 of the intensity modulation optimization with the contour segment differential. The iteration 82 is performed using the output 64 of the intensity modulation optimization operation 62 as a starting value. Since the differential change $\Delta_{CS}$ is small and affects only the selected contour segment, the output 64 is expected to be close to the "correct" value that would be produced by multiple iterations. Accordingly, the output 84 of the single iteration 82 subtracted from the output 64 (and optionally divided by the differential $\Delta_{CS}$) as per a subtraction operation 86 is expected to provide a reasonable estimate of the partial derivative of the output respective to the selected contour segment. A more complex difference metric may alternatively be used in place of the subtraction operation 86 for the purpose of the contour segment impact classification 70. Moreover, because only the single iteration 82 is performed, the partial derivative estimation operation 68 is efficient. Although a single iteration 82 is illustrated, in other embodiments two or more iterations maybe performed, either in an open-loop fashion or with iteration until a chosen stopping criterion is met.

With returning reference to FIG. 2, the impact analysis 66, 68, 70 is performed after each contour segment update operation 76. In this way, the user observes the impact of contouring operations on the intensity modulation optimization substantially in real-time, that is, during the contouring process, including any changes in the impact of various contour segments on the intensity modulation optimization that may occur during the contouring process. However, in some radiation therapy applications the contour segment impact is not expected to change significantly during the contouring process, and accordingly it may be practical to pre-calculate the impact of the various contour segments on the intensity modulation optimization. This can be done, for example, based on previous contouring/radiation therapy planning sessions performed for the present subject or for previous subjects. The pre-calculated impact can also be based on a first principles analysis, for example using an attenuation model.

Figure 8:
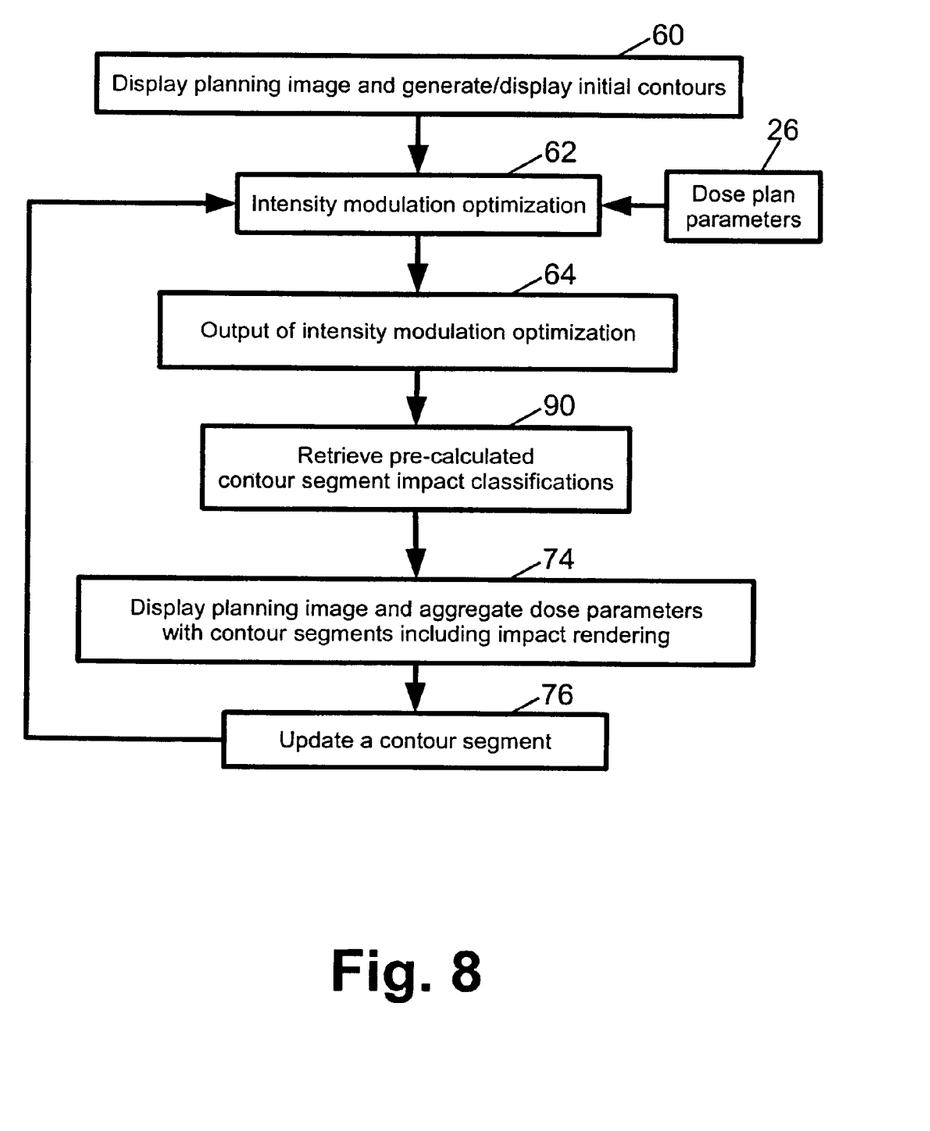
FIG. 8 diagrammatically shows a variant of the method of FIG. 2 which employs pre-calculated contour segment impact classifications.

With reference to FIG. 8, a variation of the process of FIG. 2 is shown. The process of FIG. 8 differs from that of FIG. 2 in that the impact analysis operations 66, 68, 70 are replaced by a retrieval operation 90 that retrieves pre-calculated contour segment impact classifications that are then used by the display sub-module 24 in the display operation 74 in order to display the contours coded by impact on the intensity modulation optimization. In the embodiment of FIG. 8, the coding of the contours is based on the pre-calculated contour segment impact classifications. This approach is suitably applied for a class of planning tasks that are sufficiently similar that the pre-calculated contour segment impact classifications apply.

The disclosed contouring approaches with impact coding of contours involves calculating and analyzing the treatment plan as .a part of the contouring process. The radiologist or other medical professional performing the contouring benefits by receiving visual "importance" feedback during the manual contouring, or by integrating an importance feature along the contours into an automated segmentation algorithm in the case of automated or semi-automated contouring. In some embodiments, the contour impact coding is input to an automated segmentation/contouring algorithm, which allows for relaxation of the accuracy requirements of the automated algorithm. In manual contouring, the technician is informed of which areas of the initial contour delineation need to be improved. The intensity modulation optimization sub-module 30 is complemented by the differential analysis sub-module 40 to enable estimation of the partial derivatives with respect to contour segments. As noted with reference to FIG.

7, the differential analysis sub-module 40 optionally estimates the partial derivatives in a first approximation. by a fast numerical scheme, for example using a single iteration of the intensity modulation optimization.

Other variants are also contemplated. For example, the radiologist can first make a quick, sketchy outline of the tumor (or other radiation target region) and all risk organs (or, more generally, risk regions). Then the treatment plan is calculated and analysed, in particular the differential analysis with respect to the contours is undertaken. The results of this analysis assign a quantitative "impact" value for each contour segment with respect to the change of the plan/dose deposit. The different impact values can be coded in the display using color-coding, or line-type coding, or line thickness coding, or so forth, so as to indicate where the contouring should be more or less precise. When the technician updates a contour (for example, using a point and drag operation by operating a mouse or trackball), the differential dose calculation is redone and the contour color-coding is updated.

For some applications, such as prostate treatment planning where the radiation target region is the prostate and the risk regions to be delineated typically include femur heads, the bladder, and the rectum, certain contour segments are unlikely to have high impact regardless of the accuracy of delineation, while other contour segments need to be quite accurate. In such applications, the variant approach described with reference to FIG. 8 may be employed, in which impact values are pre-calculated beforehand (for example, trained beforehand by a number of test cases). In an approach employing automated or semi-automated segmentation, the learned or pre-calculated impact values become part of (i.e., a priori knowledge included in) the model used for automated or model-based segmentation. During the model-based segmentation process the impact values are used as an additional (probabilistic) feature to balance accuracy in areas where contours are difficult to delineate. In such embodiments the calculation of dose during the segmentation can optionally be avoided.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

Having thus described the preferred embodiments, the invention is now claimed to be:

1. A method comprising:
   performing contouring to define contours delineating a radiation target region and one or more risk regions in a planning image; and
   during the contouring, displaying a planning image and the contours, the displaying including coding the contours to indicate impact of the contours on an output of an intensity modulation optimization.

2. The method as set forth in claim 1, wherein the displaying comprises color coding the contours to indicate impact of the contours on an output of an intensity modulation optimization.

3. The method as set forth in claim 1, wherein the performing of contouring comprises receiving a manual update of a contour segment and the displaying comprises updating the coding of the contours after each manual update.

4. The method as set forth in claim 1, wherein the performing of contouring comprises updating a contour segment and the displaying comprises updating the coding of the contours after each contour segment update.

5. The method as set forth in claim 1, wherein the contours comprise contour segments and the coding comprises:
   estimating partial derivatives of the output of the intensity modulation optimization respective to the contour segments; and
   coding the contour segments based on the estimated partial derivatives.

6. The method as set forth in claim 1, wherein the contours comprise contour segments and the coding comprises:
   retrieving pre-calculated contour segment impact classifications, wherein the coding comprises coding the contour segments in accordance with the retrieved pre-calculated contour segment impact classifications.

7. The method as set forth in claim 1, further comprising:
   after the contouring, performing the intensity modulation optimization to generate a radiation therapy plan complying with dose plan parameters indicative of dosage or dosage constraints for the radiation target region and the one or more risk regions.

8. A digital processor configured to perform a method as set forth in claim 1.

9. A non-transitory computer-readable storage medium storing instructions executable by a digital processor to perform a method as set forth in claim 1.

10. A method comprising:
    performing contouring to define contour segments delineating a radiation target region and one or more risk regions in a planning image;
    performing intensity modulation optimization using the contour segments to generate a radiation therapy plan and a corresponding calculated radiation dose map; and
    during the contouring, displaying the planning image and the contour segments with the contour segments coded with respect to impact of the contour segments on the intensity modulation optimization.

11. The method as set forth in claim 10, wherein the displaying comprises:
    displaying the contour segments with the contour segments coded by color or line type with respect to impact of the contour segments on the intensity modulation optimization.

12. The method as set forth in claim 10, further comprising:
    estimating partial derivatives of an output of the intensity modulation optimization respective to the contour segments; and
    computing the impact of the contour segments on the intensity modulation optimization based on the estimated partial derivatives.

13. The method as set forth in claim 10, further comprising:
    retrieving pre-calculated contour segment impact classifications indicative of the impact of the contour segments on the intensity modulation optimization, the displaying including coding the contour segments in accordance with the pre-calculated contour segment impact classifications.

14. The method as set forth in claim 10, wherein;
    the contouring comprises performing successive contour segment updates, and
    the displaying includes updating the coding of the contour segments with respect to impact of the contour segments on the intensity modulation optimization after each contour segment update of the contouring.

15. A method comprising:
    calculating a radiation dose map complying with dose plan parameters indicative of dosage or dosage constraints for a radiation target region and one or more risk regions by an intensity modulation optimization having as input at least contours delineating the radiation target region and the one or more risk regions; and rendering the contours on a displayed planning image including coding the contours to indicate impact of the contours on the intensity modulation optimization.

16. The method as set forth in claim 15, wherein the coding comprises:

color-coding the contours to indicate impact of the contours on the intensity modulation optimization.

17. The method as set forth in claim 15, further comprising:

performing contouring of the radiation target region and the one or more risk regions by iterative contour adjustment, wherein the calculating and the rendering are repeated after each iterative contour adjustment.

18. The method as set forth in claim 15, wherein the contours comprise contour segments and the coding comprises:

estimating partial derivatives of an output of the intensity modulation optimization respective to the contour segments;

computing contour segment impact classifications for the contour segments based on the estimated partial derivatives; and coding the contour segments with the contour segment impact classifications.

19. The method as set forth in claim 15, wherein the contours comprise contour segments and the coding comprises:

coding the contour segments with pre-calculated contour segment impact classifications.

20. An apparatus comprising:

a contouring module configured to iteratively adjust contours delineating a radiation target region and one or more risk regions in a planning image;

an intensity modulation optimization module configured to generate a radiation therapy plan conforming with dosage or dosage constraints for the radiation target region and the one or more risk regions delineated by the contours; and a differential analysis module configured to invoke the intensity modulation optimization module to estimate partial derivatives of an output of the intensity modulation optimization respective to the contours;

wherein the contouring module is configured to invoke the differential analysis module after each iterative contour adjustment to estimate the partial derivatives respective to the contour segments and to render the contour segments on a display of the planning image with the contour segments coded based on the estimated partial derivatives to indicate impact of the contour segments on the intensity modulation optimization.

\* \* \* \* \*